United States Patent

Rozema et al.

[11] Patent Number: 6,002,484
[45] Date of Patent: Dec. 14, 1999

[54] PHASE CONTRAST ABERROSCOPE

[76] Inventors: Jos J. Rozema, Vision lab-Department of physics-RUCA Groenenborgerlaan, 171, Antwerpen, Belgium, 2020; Dirk van Dyck, 37, Kleine Grippe, Aartselaar, Belgium, 2630; Frans J. Van de Velde, 2 Hawthorne Place, Apt. 15-0, Boston, Mass. 02114

[21] Appl. No.: 09/336,329

[22] Filed: Jun. 18, 1999

[51] Int. Cl.[6] .................................................. G01B 9/02
[52] U.S. Cl. .......................................... 356/354; 356/359
[58] Field of Search .................................. 356/354, 359, 356/360

[56] References Cited

U.S. PATENT DOCUMENTS 5,638,176  6/1997  Hobbs et al. ........................... 356/355

*Primary Examiner*—Robert H. Kim

[57] ABSTRACT

A wavefront aberration measuring device and method is based on the principles of phase contrast interference. A particular application is the two-dimensional representation of the complex optical aberrations of the complete eye optics. This device consists of an illuminating optical part, to project an image of an annular light source on the retina of the eye. This projected image becomes a secondary light source on the retina that transilluminates in reverse the eye optics. Because of imperfections in the eye optics, some phase distortions will be added to the reflected light. In the analyzing part of the device, this reflected light is optically transformed with the help of a phase plate. The resulting interference pattern is visualized with the observational part of the device and further digitally processed in order to display the optical aberrations without the need for an extensive polynomial analysis. An optional fixation device can be added to control the direction of gaze of the eye. Additionally, the instrument can be mounted on a conventional slitlamp or operating microscope.

5 Claims, 8 Drawing Sheets

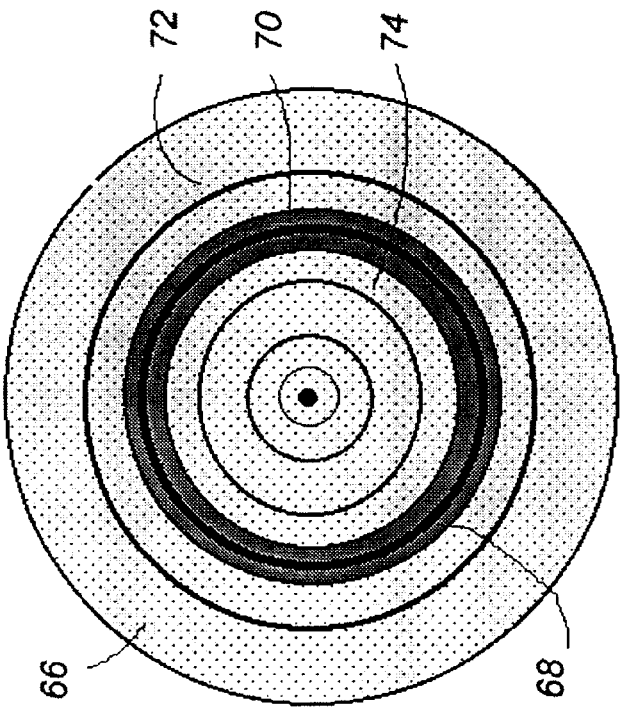
FIG. 4b
FIG. 4a
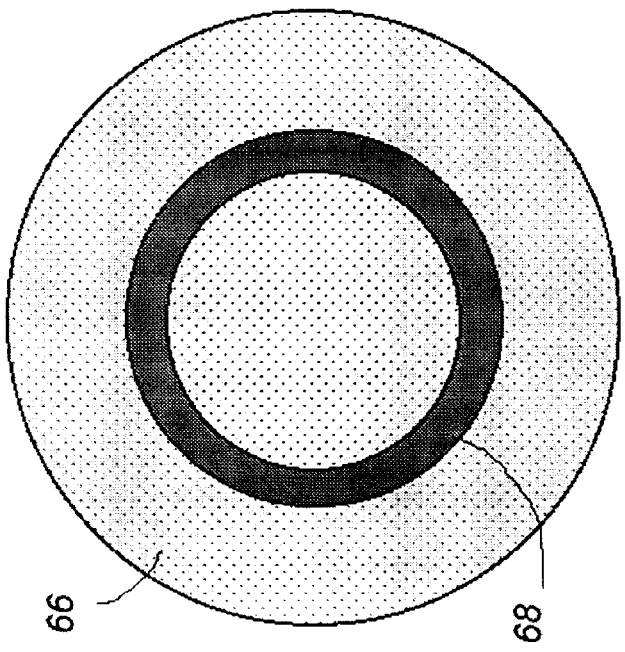
FIG. 4c

PHASE CONTRAST ABERROSCOPE

BACKGROUND—FIELD OF INVENTION

The invention relates generally to instruments and methods for examining the human eye and specifically to the measurement of the optical aberrations of the human eye optics using the phenomenon of phase contrast.

DESCRIPTION—DESCRIPTION OF PRIOR ART

All practical optical constructions, including the human eye, exhibit some degree of distortion that influences the quality of the image formed by this system. In general, these distortions are called wavefront aberrations.

Over the last decades, many different methods for the visualization and measurement of wavefront aberrations of the human eye have been proposed. Existing methods can generally be classified into two groups.

The first group is very diverse and comprises of all kinds of different configurations of interference devices such as the Mach-Zehner interferometer or the Michelson-Morley interferometer. These instruments produce a complex pattern of darker and brighter areas that may be transformed into an aberration map of the eye.

The second group comprises methods using the Hartmann-Shack device as proposed by Liang and Williams, and the spatially revolved autorefractometer as proposed by Penney and Webb. Liang and Williams use a wide laser beam perpendicularly incident onto the cornea and focused to a small spot on the retina. This spot is now considered a secondary coherent light source, which backscatters out of the eye. Because of imperfections in the eye optics, some phase distortions will be introduced in the wavefront that is generated by the spot. These phase differences can be detected with a planar array of lenslets, also called a Hartman-Shack plate, that focus each on a portion of the light coming back from the eye. The spatial deviations of the individual focus spots generated by each of the lenslets with respect to a pattern of focus spots that would be generated by an ideal plane wave, are used to determine the gradient of the wavefront distortion. The method of Penney and Webb, initially formulated by Smirnov and continued by Van de Velde, uses parallel pencils of light that are incident on the cornea. In the presence of aberrations, such parallel beams will focus on the retina in slightly different locations from the ideal unique focus spot if no aberrations were present. These locations can be determined by imaging or psychophysical means. From the slope measurements of both methods, an aberration map can be constructed using a well-known fitting procedure with Zernike polynomials.

Another distinct group of methods that would be useful to measure the wavefront aberrations of the eye comprises methods that generate an optical transform of the light that is scattered by the optics of the eye. This optical transform could be accomplished by putting a Ronchi-grating, a raiser edge, an opaque spot or ring, or a phase plate in the focus of a lens that captures the backscattered light from the retina. The proposed Phase Contrast Aberroscope or PCA can be situated in this group. Until now, the phase contrast method as originally developed by Zernike, has been used with considerable advantage to image anatomical detail in biological objects that do not exhibit a significant variation in absorption of light. Such phase objects that are only different in spatial variations of refractive index, are commonly found in living tissues. The eye is no exception, and consequently a phase contrast method for the purpose of imaging the anatomy of the retina and other ocular structures has been proposed by Thall.

OBJECT, SUMMARY AND ADVANTAGES OF THE INVENTION

It is therefore an object of the invention to apply the principles of phase contrast imaging to the measurement of the wavefront aberrations of the human eye optics. In order to achieve this goal, the basic setup of the phase contrast microscope as proposed by Zernike is adapted. The illuminating optical part of the device is used to project an annular image of the light source on the retina. This light source can emit in the infrared range of the spectrum. As in the Hartmann-Shack method, this projected image is becomes a secondary light source on the retina that transilluminates in reverse the eye optics. Due to wavefront aberrations that are present in the eye optics, the light from this source acquires phase distortions. In a second step, the analyzing part of the aberroscope e is used to translate these phase differences into amplitude differences that are visible to a highly sensitive CCD camera or other observation device. The image that is likewise obtained, consists of adjacent fringes of variable contrast, that may be thought of as repetitive contour plot lines of the aberration surface over a 2 pi interval. Using a simple phase continuation procedure, these lines can then be modified to represent the true two dimensional aberration surface of the eye optics, without the need for further polynomial curve fitting analysis.

Major advantages of the instrument and method of measurement of wavefront aberrations are the relative simplicity and versatility of the device, and the direct visualization of the optical aberrations of the eye optics without the need for further extensive mathematical extrapolations.

BRIEF DESCRIPTION OF THE DRAWINGS

FIGS. 4a, b and c show how the reflected light will pass through the quarter wave phase plate and how the different orders within the focused light are distributed.

REFERENCE NUMERALS OF THE DRAWINGS

Figure 1:
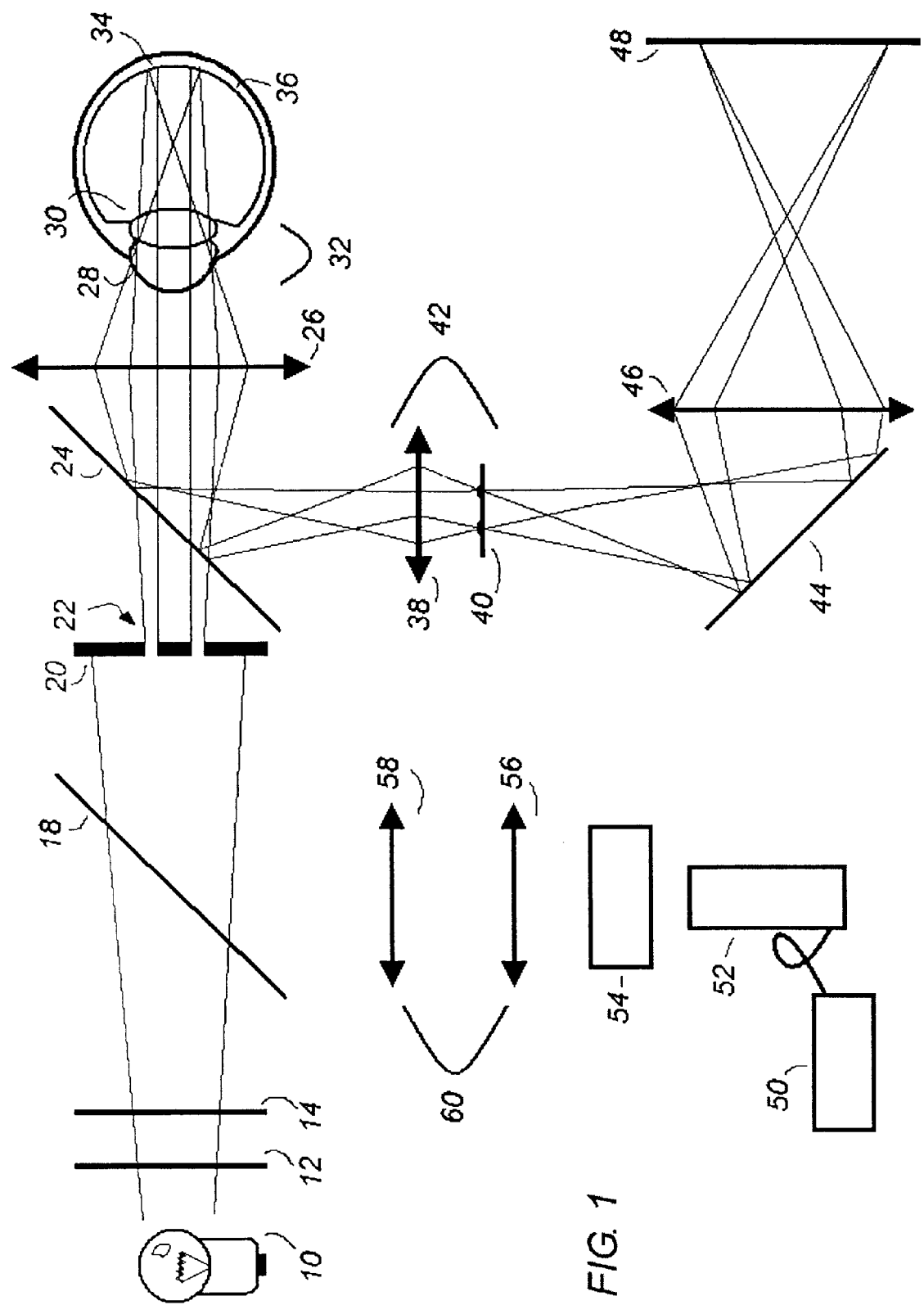
FIG. 1 shows the phase contrast mode and the basic setup of the embodiment including illuminating, analyzing and observational parts.

10 light source
12 infrared filter and optional set of crossed polarizers
14 diffuser
18 beam splitter
20 screen
22 annular opening with central stop
24 beam splitter
26 lens element
28 cornea of the eye 30 lens of the eye
32 complete set of dioptric surfaces within the human eye
34 image of the annular opening 22 on the retina of the eye
36 retina of the eye
38 lens element
40 phase plate
42 analyzing part of the device, comparable to a microscope objective
44 mirror element
45 lens element
46 lens element
48 observation screen or CCD camera device
50 laser or LED driver
52 laser or LED
54 acousto-optical deflector
56 lens element
58 lens element
60 combination of 56 and 58, acting as a beam expander
62 fixation point on the retina
64 circular patch of light on the retina
66 glass substrate of the phase plate
68 quarter wave groove on the phase plate
70 position of maximum intensity of zeroth order diffracted light
72 position of maximum intensity of outer first order diffracted light
74 position of maximum intensity of inner first order diffracted light
76 illuminating part of a conventional slit lamp or biomicroscope
78 eye piece
80 observational device, CCD camera
82 head support for the subject
84 phase contrast module
86 annular mirror
88 Wollaston prism
90 glass plate
92 non reflecting surface of the mirror
94 reflecting surface of the mirror
96 glass plate
98 glass plate
100 umbrella shaped structure, a number of rods and deformable membrane
102 ring with lead screw
104 ring shaped element
106 handle for adjusting the diaphragm size
108 handle for controlling the umbrella shaped part
110 blades of the diaphragm
112 rod with lead screw
114 axis of the blades of the diaphragm

DETAILED DESCRIPTION AND OPERATION OF A PREFERRED EMBODIMENT

Figure 2:
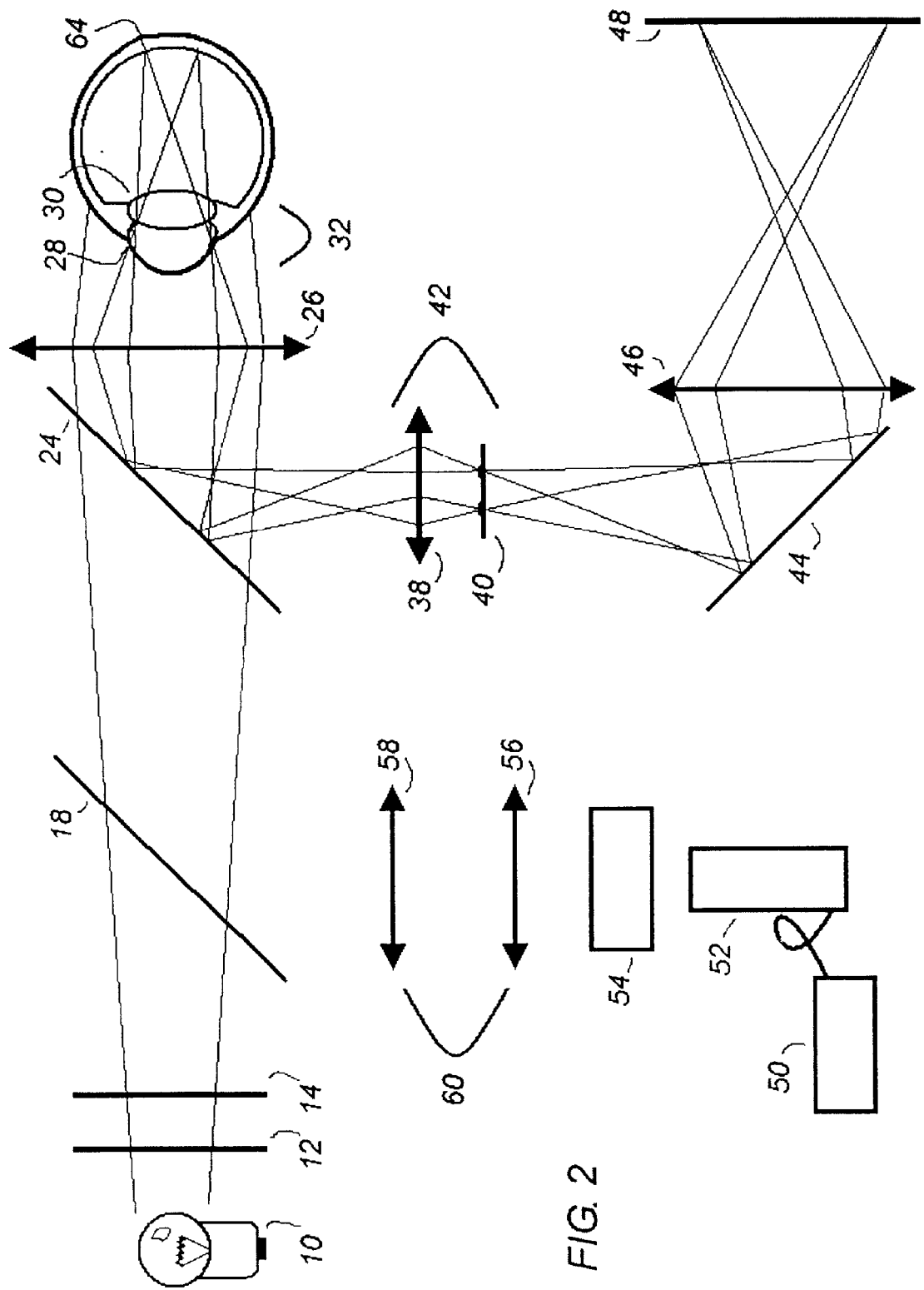
FIG. 2 shows the full light mode.

A complete setup of the invention will work in two different modes, respectively illustrated in FIGS. 1 and 2 as the phase contrast mode and the full light mode.

In FIG. 1, the basic components of the embodiments including illuminating part, analyzing part and observational part, are used for the phase contrast mode. A light bulb 10, combined with an infrared filter 12 will serve as an infrared source. The light from this filament source passes the diffuser 14 to obtain an even intensity, and then a beam splitter 18. A screen 20 with an annular opening and central stop 22 is placed in the optical path. At this point, the illuminating part produces an infrared, non-coherent, diffuse and ring shaped bundle of divergent light.

A lens 26 is placed in such manner that both the opening 22 and the retina 36 of the eye are situated in confocal planes. As a result, an image 34 of the annular opening 22 is projected on the retina 36. The image 34 and the annular ring 22 are therefore conjugate and in focus. The image 34 on the retina becomes a secondary annular light source that transilluminates in reverse the internal structures of the human eye comprising the lens 30 and the cornea 28. When passing through the combined dioptric surfaces 32 inside the eye, the returning light acquires some phase distortions as a result from the optical aberrations that are invariably present. The aberrated light returns through the lens 26, is further redirected with the help of a beam splitter 24, and separates into several different orders of diffraction. In the analyzing part of the device, the zeroth order diffraction light is focused on a ring shaped quarter wave portion 68 of plate 40 with the help of a lens 38 and as a result its phase is shifted. Its relatively high intensity can also be reduced by the phase plate. The higher orders of diffracted light will pass through the phase plate 40 with their phase essentially unaltered. To obtain such a difference between the zeroth and higher orders of diffraction, the ring shaped quarter wave portion of phase plate 40 must correspond as close as possible to the image of the secondary light source on the retina 34. This is illustrated in FIG. 4. According to the theory of Zernike, the optimal separation of diffraction orders and resultant phase shift are essential to obtain a high quality phase contrast interference pattern. In a third step, the transformed light from the phase plate 40 is reflected by a mirror 44 and focused by means of a lens element 46 onto a screen or a CCD camera device 48. As a result of interference, the observation part of the device displays a two-dimensional map of shades of gray that represents the wavefront aberrations of the eye at its exit pupil.

The second full light mode, as illustrated in FIG. 2, is essentially similar to the phase contrast mode of FIG. 1, except for the removal of screen 20 with the annular opening 22. Now the secondary light source at the retina 64 has a full circular shape instead of an annular shape. This results in a loss of the phase contrast effect because the shape of the secondary light source 64 and the quarter wave plate 40 are no longer correspondent. The resulting image on the screen 48 will be amplitude dependent, showing only the degree of absorption of light in the different regions of the exit pupil of the eye optics 32.

Figure 3:
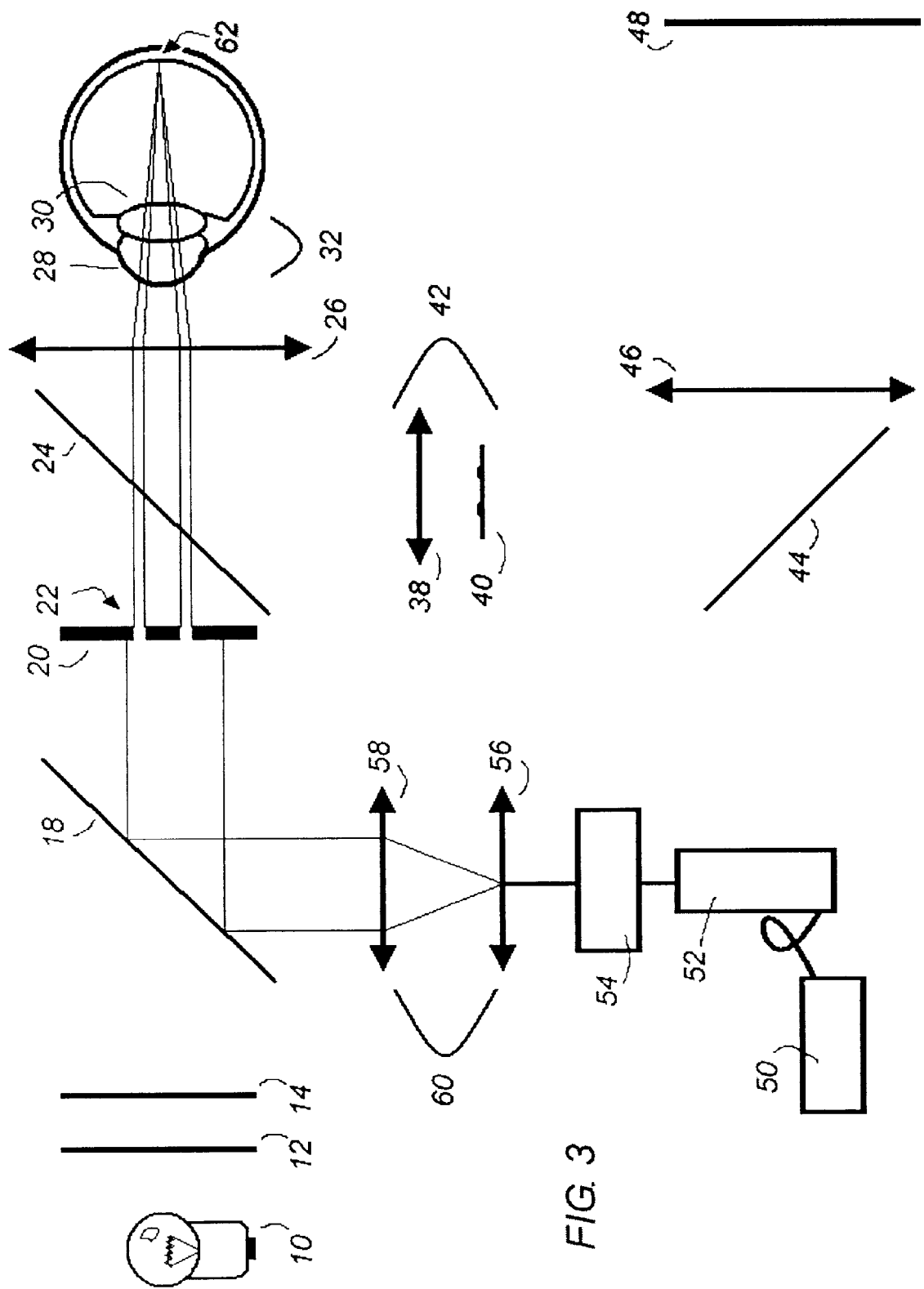
FIG. 3 illustrates the implementation of a fixation point mode.

As illustrated in FIG. 3, a fixation point 62 can be projected on the retina 36 during testing. This adjustable fixation point allows the subject's eye to turn in a controlled manner, so that a region of interest in the eye optics 32 will become more visible. The light beam originates from a diode laser or a LED 52 and is controlled in intensity by the driver 50. A computer driven acousto-optic deflector 54 is used to angulate the beam. This is followed by a beam expander-telescope 60 with adjustable lenses 56 and 58, a combining element 18, the screen 20 with the annular opening 22, a beam splitter 24 and the lens 26. When the position of the lens 26 and telescope 60 have been properly adjusted, the subject will see this light beam as a small circular spot of light 62. This can be accomplished psychophysically by asking the subject whether s/he sees a ring, blurred disc or a fine dot. In case s/he sees a ring or a blurred disc, the position of the lenses must be adjusted by the operator until the light spot on the retina is as small as possible.

The switching between the phase contrast mode and the full light mode is done by removing the screen 20 with the annular opening 22. The infrared light that is used to visualize the wavefront aberrations is invisible to the human eye, therefore the subject will only see the fixation spot 62.

In both modes that have been described, the exact positioning of lenses 26 and 38 is crucial. They must be placed in such manner that the annular opening 22, images 34, 62 and 64 on the retina, and the quarter wave plate 40 are all confocal. As mentioned before, only when the zeroth order matches the ring 68 on the quarter wave plate 40, can a good phase contrast be obtained. Therefore it is necessary to initialize or calibrate the device, prior to the measurements, to assure as much as possible this confocality and similarity in size. This initialization can be accomplished in a number of ways.

The setup from the phase contrast mode of FIG. 1 can be used to position lens 26. The infrared filter 12 is replaced by a set of rotating polarizers to allow a attenuated visible light beam to enter the eye. Now the subject must indicate whether the ring shaped image 34 of the projected light beam is as sharp as possible.

The best positioning of lenses 26 and 38 can also be found out by examining the shape of the light beam coming from the reflection of images. This reflected light can be processed as described in the phase contrast mode. Adjustment of the lens 26 will now result in a sharp image on the screen or CCD-camera. This approach eliminates the subjective nature of a psychophysical adjustment by the subject as previously described.

The phase contrast principle assumes that the image of the annular opening on the retina 34, is considered a secondary light source, that is also perfectly annular. This annular shape is very important since the shape of the secondary light source 34 must correspond as much as possible to the annular shape of the quarter wave portion 68 of plate 40. This implies that the wavefront aberrations in the eye optics 32 may not be too variable.

Assuming that the amplitude of the incident light on the aberrated eye optics 32 is unity, and that $\phi(r)$ is the aberration function of the eye, then the amplitude of the plane wave function $\psi(r)$ after passing the eye optics 32 has to be multiplied with the factor $e^{i\phi(r)}$, so it becomes:

$$\psi(r)=1 \cdot e^{i\phi(r)} \quad (1)$$

The wave function at the retina $\psi'(k)$ will be the Fourier transform of (1):

$$\psi'(k)=\Im(e^{i\phi(r)}) \quad (2)$$

and for the intensity of this image on the retina 34, the squared modulus must be taken:

$$I(k)=|\Im(e^{i\phi(r)})|^2 \quad (3)$$

This intensity will serve as secondary light source 34 and illuminate the aberrated eye optics 32 from behind. The wave function $\psi''(r)$ that reaches the eye lens 30 will then be:

$$\psi''(r)=\Im|\Im(e^{i\phi(r)})|^2 \quad (4)$$

This can be written as:

$$\psi''(r)=e^{i\phi(r)}*e^{-i\phi(-r)}=\tfrac{1}{4\pi i}s\int e^{i(\phi(r')-\phi(r'-r))}dr' \quad (5)$$

This integral is easily solved if we assume that the differences in wavefront aberrations are not too large. In that case, the weak phase approximation can be applied as follows:

$$E^{i(\phi(r')-\phi(r'-r))}\approx 1+i\phi(r')-i\phi(r'-r) \quad (6)$$

So (5) becomes:

$$\psi''(r)=\tfrac{1}{4\pi i}s\int(1+i\phi(r')-i\phi(r'-r))dr' \quad (7)$$

Since the aberrations do not vary too much, we may also assume:

$$\int i\phi(r')dr'=\int i\phi(r'-r))dr' \quad (8)$$

And after combining this with equation (7) it becomes:

$$\psi''(r)\approx 1 \quad (9)$$

In other words, when the wavefront aberrations are not varying too much, i.e. if their differences are small compared to unity, then, for our purpose, the intensity distribution of the light that comes back from the retina is almost the same as the distribution that fell into the eye.

In FIG. 4a the quarter wave plate is shown. It consists of a glass or a plastic plate 66, in which a annular groove 68 has been cut. This cutting can be done in two ways. The groove can be cut in the glass, which results in a phase advancement of the incident wave. Also the glass can be cut away around the annulus, which results in a wave retardation. Practically, the combination of a lens 38 and the quarter wave plate 40 resemble a microscope objective 42.

When the device is used in the phase contrast mode, the reflected and aberrated image of the secondary light source on the retina 34 is projected on the quarter wave plate 40 as shown in FIG. 4b. In this figure only the position of the maximum intensity of the zeroth order of diffraction 70 is drawn. This is also the case for the inner 74 and outer position of the first diffraction order 72. In reality, many higher orders are present and the different orders are found in concentric rings with a mutually overlapping Gaussian profile as in FIG. 4c. This makes them very hard to separate from each other. The quarter wave plate is constructed in such manner that only the zeroth order and as little of the higher orders as is possible will fall on the annulus 68 and will thereby undergo a phase shift. The higher orders will pass unaltered. As is shown in equation (9), the shape of the incident light beam $\psi(r)$ and the beam returning from the eye $\psi''(r)$ are almost equal. So this will pose no problem for the agreement between the shape of the secondary light source 34 and the shape of the phase plate groove 68.

In other embodiments, the quarter wave plate may be substituted by a plate with a dark ring of with a raiser edge, this in order to obtain dark field images.

Due to the wavefront aberrations that are inherent to the different components of the device, a regular examination and calibration is needed. This can be done by placing an optically flat mirror with known aberrations of less than $\lambda/10$, in stead of the eye, in front of the device and measure the wavefront aberrations in the way described above. Later, these aberrations can be digitally subtracted from the end result.

The final image on the screen 48 will look like a set of neighboring interference fringes. They represent contour plot lines of the two dimensional aberration surface $\phi(x,y)$. Each fringe is a interval of $\phi(x,y)\epsilon[0,2\pi]$. Once the phase difference $\phi(x,y)$ reaches $2\pi$, it will drop back to zero. This results in a saw tooth view of the surface.

A first mathematical treatment of this saw tooth image will consist of a phase continuation procedure, in which the different adjacent phase fringes are made continuous by adding the value of 2 pi. This will result in a smooth two dimensional view of the wavefront aberrations across the eye optics 32. In order to enumerate the aberrations, it is necessary to calibrate the gray scale values with a phase plate of which the properties are known.

Another possibility is the fitting of the aberration surface with a set of Zernike polynomials. These orthonormal polynomials are regularly used for these purposes and can easily approximate the lowest order Seidel primary wavefront aberrations, such as defocus and astigmatism. These two types of aberrations can be corrected with ordinary lenses. It is possible with the phase contrast mode to invert the information of the two dimensional map of aberrations, without the need of a polynomial analysis. This inverted information can be etched on a glass plate or a contact lens. In this manner, also the higher orders of aberration could be corrected.

Ramifications and other embodiments

Figure 5:
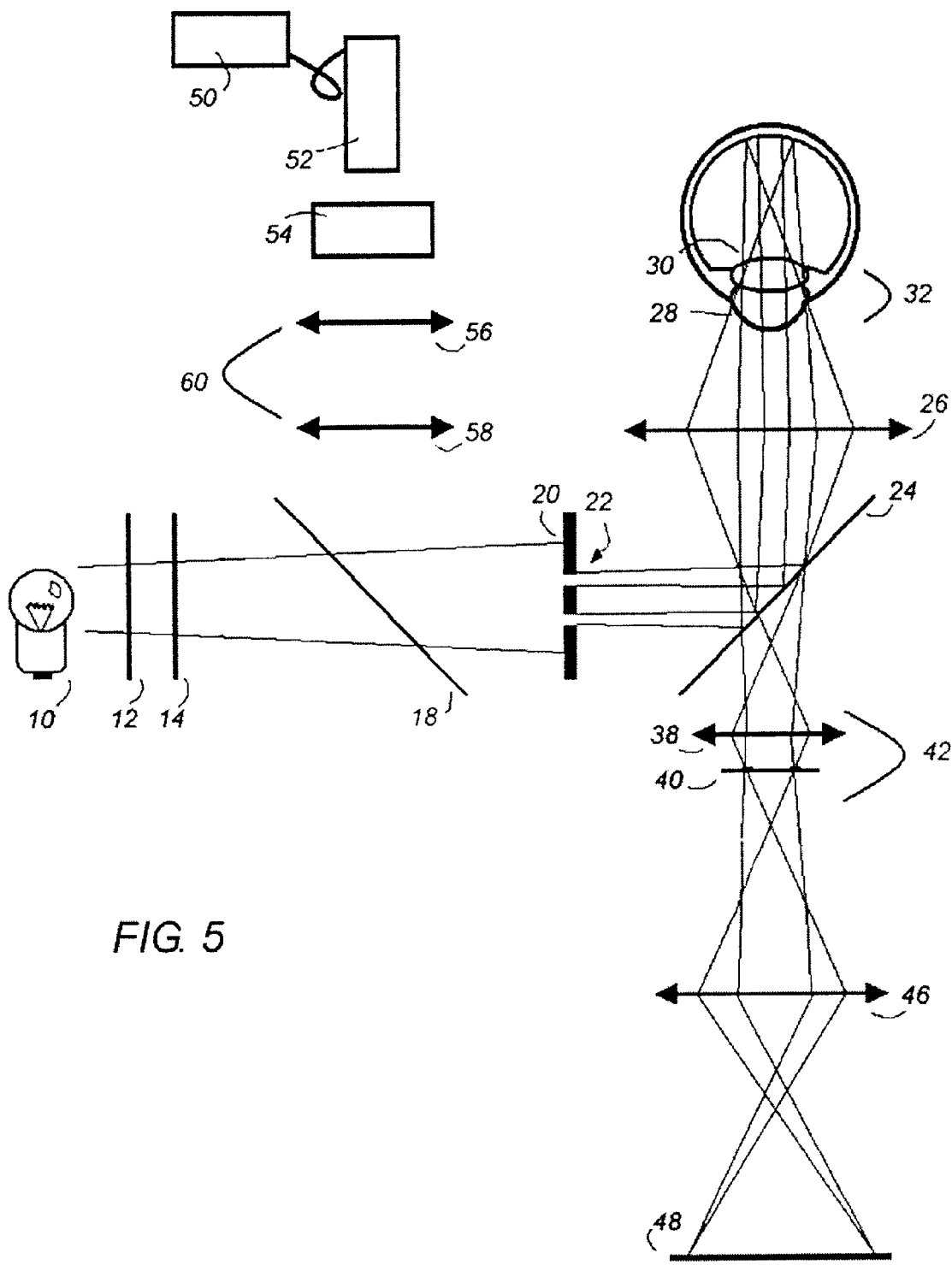
FIG. 5 demonstrates an alternative setup of the embodiment, in which the optical path of the illuminating and observational part of the device are switched.
Figure 6A:
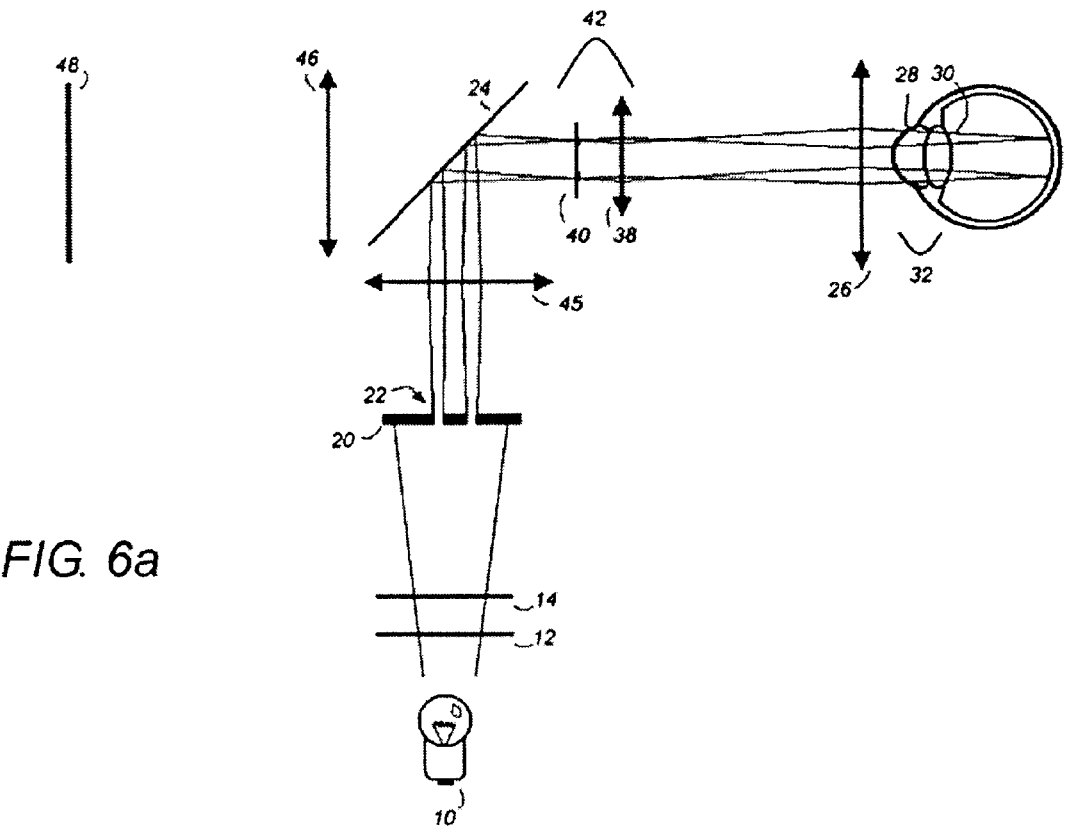
FIGS. 6a and b show an alternative setup of the invention in which the illuminating optical path is passing the quarter wave plate.
Figure 6B:
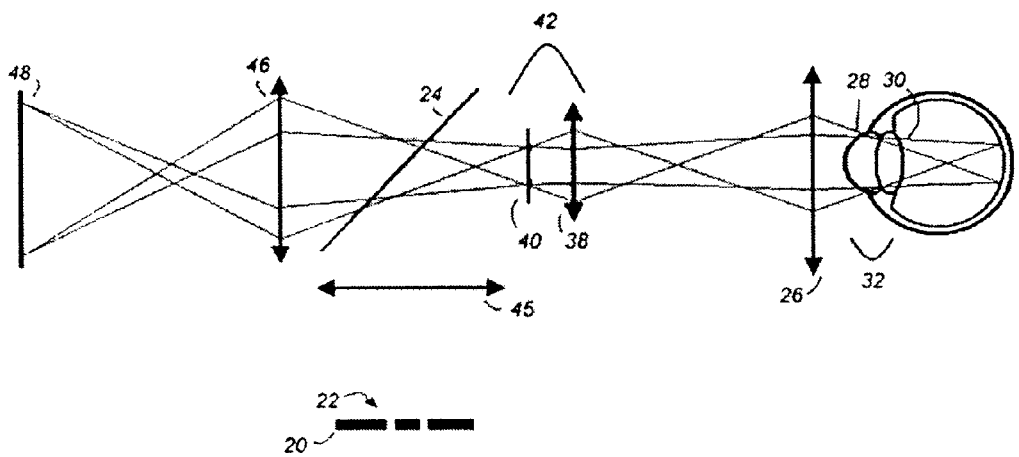

The device can be adapted in many different ways as illustrated in FIGS. 5 and 6.

In FIG. 5 the optical path of the light that illuminates the eye and the path of the observational path are switched. This can eliminate some spurious reflections in the image that are caused by some type of beam splitters.

FIGS. 6a and b show a setup in which the annular illumination beam passes the quarter wave plate 40, before it enters the eye. To get this accomplished, a new lens 45 must be placed between the screen 20 with the annular opening 22 and the beam splitter 24, this in order to project an image of the annular opening on the quarter wave plate 40. The remainder of the setup is analogous to the embodiment of FIG. 1.

Figure 7B:
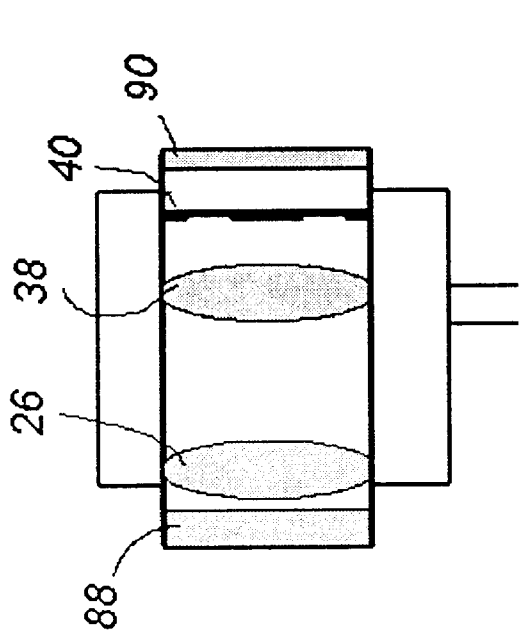
FIGS. 7a, b and c show the device mounted on a conventional slitlamp.
Figure 7C:
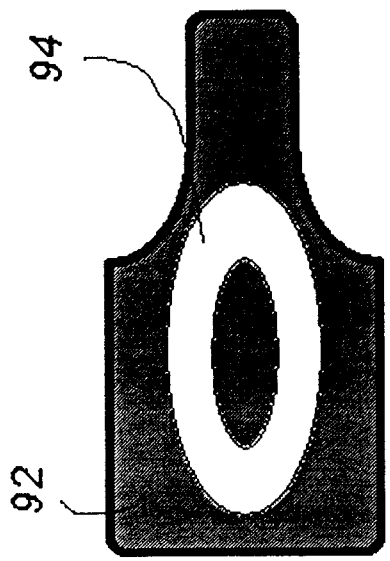
Figure 7A:
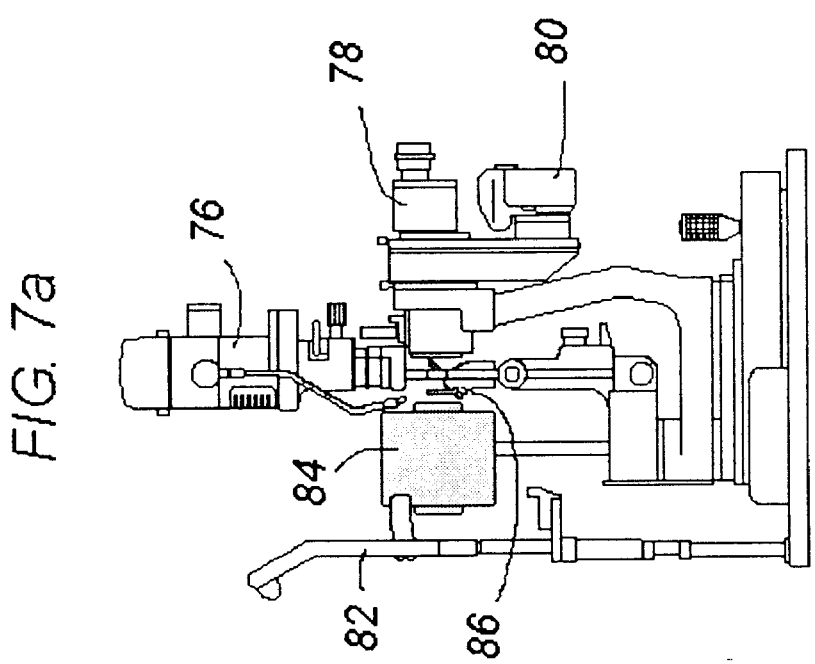

The setup of FIG. 7 is a variation of the one that is illustrated in FIG. 6. Here the device is no larger than a small module that can be mounted on a slit lamp. This slit lamp already contains most of the components needed for the phase contrast aberroscope. As can be seen in FIG. 7a, both the illuminating system 76 and CCD camera 80 or an eye piece 78 are already present, as well as a head and chin support 82 for the subject. The only adaptations of the slit lamp will consist of the addition of a small module 84 and a new and special mirror 86. The extra module 84 in FIG. 7b consists of a Wollaston prism 88, two lenses 26 and 38, the quarter wave plate 40 and a glass plate 90 for protection purposes.

Figure 8A:
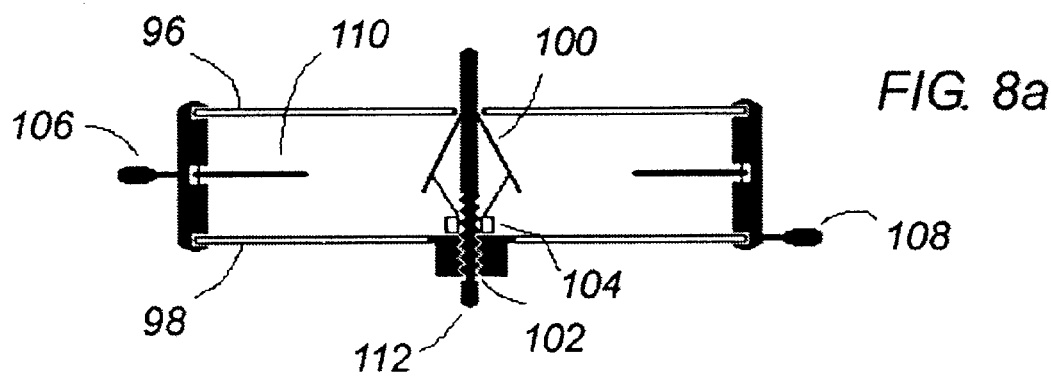
FIGS. 8a and b illustrate an annular diaphragm that is able to adjust the diameter of both the inner and the outer rim of the ring.

A new part that needs to be described is the special mirror 86 in FIG. 7c. This mirror has an elliptical annular reflecting surface 94, surrounded by a non reflecting surface 92. Since this mirror is placed under an angle of 45 degrees with respect to the incident light, the light reflected by this mirror will form a round annular light beam, analogous to the beam that emerges from the annular opening 22 in FIG. 6. An annular beam might also be obtained by introducing a ring shaped diaphragm in the illuminating system 76. Such a diaphragm is shown in FIGS. 8a and b. The rest of this setup works completely analogous to the one described in FIG. 6.

Figure 8B:
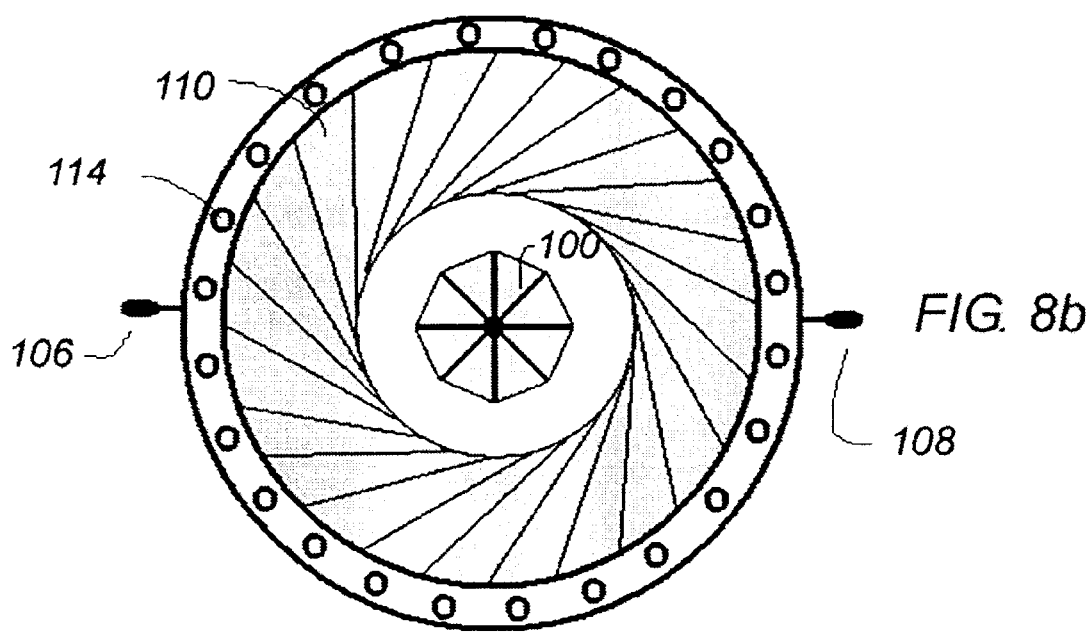

The annular diaphragm, as shown in FIG. 8 has the special property that it is capable of changing its diameter of the inner edge or rim as well as the diameter of the outer edge. The construction consists of a regular diaphragm 110 with a handle 106. The diameters that can be used with this diaphragm are limited to specific values. Behind this diaphragm and in front of it, small glass or plastic plates 96 and 98 are placed. In the center of plate 98 a ring shaped reinforcement 102 with a lead screw 112 can be rotated by the operator. On this rod 112, little rods 100 are capable of turning around. In between these little rods 100 an expandable membrane is hung. The little rods 100 are connected to a ring 104 situated on the rod 102. The whole construction acts as an umbrella. The opening of the umbrella can be controlled by turning the glass plate 98 with the use of a handle 108. The lead screw makes the rod go up and down, which causes the umbrella to open or close. In this way both diameters of the annular opening can be adjusted. In stead of an umbrella, it is also possible to use a number of filaments, sliding over one another when the rod 112 turns around. Another possibility is the use of small rods that can be bend outwards and to which a long metal plate is attached. When the ring 104 is shifted, the rods will bend, forming a circle with the attached metal plates.

This versatile diaphragm can improve the agreement between the secondary light source 34 and the phase plate 40 when the wavefront aberrations are too large to guarantee a good agreement.

The phase contrast mode can also be used with visible light, but this has the disadvantage that the bright light will cause the pupil of the eye to contract. This can be remedied by administering some pupil widening drops in the eye before the procedure. In the case where visible light is used, the screen or the CCD-camera 48 could be replaced by an eye piece through which a direct view of the wavefront aberrations is offered.

For the fixation point in FIG. 3, a VCSEL or an array of LED's might be used in stead of the modulated laser 52 with the acousto-optical deflector 54. This can facilitate the construction of the device.

The entire part of the setup that is used for the generation and projection of the fixation point, 50, 52, 54, 56, 58, 18, could be omitted. Also the full light mode is not indispensable for the method to work.

It is also possible to add some features to the preferred embodiment:

Some of the lenses, such as 26 and 46, can be replaced by a double lens achromatic system, thus eliminating the possible distortions introduced by spherical and chromatic aberrations.

A Wollaston prism could be placed between the lens 26 and the eye to enhance the phase differences.

If the round annular phase plate is replaced by a number of elliptic annular phase plates that are tilted at a predefined angle, there would be the possibility to extend the number of higher orders that can play a role in the phase contrast phenomenon.

The glass or plastic phase plate 40 from a microscope objective 42 might be replaced by an adjustable liquid crystal screen that forms an annular phase plate able to induce a phase shift to the zeroth order diffracted light. With such a screen it is possible to switch very fast from a phase retardation mode to a phase advancement mode. When the images of both modes are combined, it is possible to get a better contrast and resolution in the display of the wavefront aberrations. In an advanced embodiment of the invention, this might lead to a three mode aberroscope combining advanced phase contrast, retarded phase contrast, the full light mode with fixation point.

In a future stage, it might be possible to adapt the device for three dimensional imaging, using parallax effects or the principles of tomography. This opens the possibility of determining the exact three dimensional location of the wavefront aberrations.

The full light mode can be used for the mapping of diseases such as cataract, in which the eye lens 30 becomes opaque. As this opacity is more transparent to infrared light, different wavelengths might be used for the imaging. These different wavelengths can be generated by using different filters 12 behind the source 10.

It is also possible to use the different embodiments described above to determine the wavefront aberrations for any optical system in general, even a single lens, by replacing the eye optics 32 with the optical system to be investigated and the retina 36 with an optical flat.

We claim:

1. A device for measuring the wavefront aberrations of an optical system consisting of a combination of optical elements, based on the principle of phase contrast interference, and said device comprising:

A. a primary illuminating source that includes a means for producing light, a set of filters and diaphragm, B. first focusing means to project said primary illuminating source through said combination of optical elements on a reflecting surface, thus creating a secondary illuminating source confocal with said first focusing means, C. a beam splitter to separate the optical paths of said primary illuminating source and said secondary illuminating source, D. an analyzing means comprising second focusing means and phase plate, said phase plate having a phase shifting area and a phase preserving area for transmitted light, thereby permitting phase contrast to occur after interference, said second focusing means and first focusing means enabling a maximum of light reflected from said secondary illuminating source to pass through said phase shifting area, thus maximizing the effect of phase contrast, E. observation means and third focusing means to display the phase contrast by interference of light from said secondary illuminating source after passing through said optical system and said phase plate; thereby enabling the calculation of the wavefront aberrations of said optical system.

2. A device for measuring the wavefront aberrations of an optical system consisting of a combination of optical elements, based on the principle of phase contrast interference, according to claim 1 which said reflecting surface is replaced by the retina of an eye, and said optical system comprises the cornea, lens and other dioptric media of said eye.

3. A device for measuring the wavefront aberrations of an optical system consisting of a combination of optical elements, based on the principle of phase contrast interference, according to claim 1, in which said primary illuminating source has wavelengths in the infrared range of the spectrum.

4. A device for measuring the wavefront aberrations of an optical system consisting of a combination of optical elements, based on the principle of phase contrast interference, according to claim 1, in which said diaphragm has an annular opening, creating a hollow bundle of incident light onto said optical system, and thereby avoiding spurious reflexes from the surfaces of said combination of optical elements.

5. A device for measuring the wavefront aberrations of an optical system consisting of a combination of optical elements, based on the principle of phase contrast interference, according to claim 1, further incorporating the improvement of a fixation means comprising second light source, directing means and fourth focusing means.

* * * * *